US012576221B2

(12) United States Patent
Stuart

(10) Patent No.: US 12,576,221 B2
(45) Date of Patent: Mar. 17, 2026

(54) NOZZLE ARRANGEMENT

(71) Applicant: Merxin Ltd, King's Lynn (GB)

(72) Inventor: Adam Stuart, King's Lynn (GB)

( * ) Notice: Subject to any disclaimer, the term of this patent is extended or adjusted under 35 U.S.C. 154(b) by 896 days.

(21) Appl. No.: 17/745,357

(22) Filed: May 16, 2022

(65) Prior Publication Data

US 2023/0364360 A1 Nov. 16, 2023

(51) Int. Cl.
| | |
|---|---|
| *A61M 15/00* | (2006.01) |
| *A61M 16/14* | (2006.01) |
| *B05B 15/50* | (2018.01) |
| *B05B 15/65* | (2018.01) |

(52) U.S. Cl.
CPC ........ *A61M 15/0001* (2014.02); *A61M 16/14* (2013.01); *B05B 15/50* (2018.02); *B05B 15/65* (2018.02)

(58) Field of Classification Search
CPC ......... B05B 15/50; B05B 15/65; A61M 16/14
See application file for complete search history.

(56) References Cited

U.S. PATENT DOCUMENTS

| | | | | |
|---|---|---|---|---|
| 5,129,579 A * | 7/1992 | Conte | ..................... | B05B 17/06 |
| | | | | 239/4 |
| 6,261,367 B1 * | 7/2001 | Donges | ................. | B05C 5/0225 |
| | | | | 156/356 |
| 7,128,283 B1 * | 10/2006 | Shahin | .................... | B05B 1/042 |
| | | | | 239/599 |
| 7,284,713 B2 | 10/2007 | Geser et al. | | |

| | | | | |
|---|---|---|---|---|
| 2003/0226907 A1 * | 12/2003 | Geser | ..................... | A61M 11/00 |
| | | | | 239/398 |
| 2007/0007370 A1 * | 1/2007 | Roman | ................... | B05B 15/50 |
| | | | | 239/599 |
| 2008/0156320 A1 * | 7/2008 | Low | ..................... | A61M 11/005 |
| | | | | 128/200.16 |
| 2009/0147049 A1 | 6/2009 | Lee et al. | | |
| 2016/0199868 A1 | 7/2016 | Ikushima | | |
| 2019/0160234 A1 * | 5/2019 | Lefkowitz | ............ | A61M 11/041 |
| 2021/0093802 A1 | 4/2021 | Rawert et al. | | |

FOREIGN PATENT DOCUMENTS

| | | |
|---|---|---|
| GB | 2542401 A | 3/2017 |
| NL | 1010831 C1 | 6/2000 |
| WO | 2005065294 A2 | 7/2005 |
| WO | 2014046906 A1 | 3/2014 |
| WO | 2015034085 A1 | 3/2015 |

OTHER PUBLICATIONS

International Search Report and Written Opinion issued for International Patent Application PCT/IB2023/055019, on Sep. 1, 2023, of 15 Pages.
Combined Search and Examination Report under Sections 17 and 18(3) issued in GB Patent Application No. GB2207090.8 on Oct. 21, 2022, 6 pages.

* cited by examiner

*Primary Examiner* — Valerie L Woodward
(74) *Attorney, Agent, or Firm* — RC Trademark Company

(57) ABSTRACT

A nozzle arrangement for delivering a liquid from a liquid delivery device includes a nozzle having an inlet side for receiving a liquid to be delivered and an outlet side for delivering the liquid. The nozzle arrangement also includes a fixing device for fixing the nozzle in the delivery device and a recess located at the outlet side of the nozzle. The recess is arranged to wick away liquid deposited on the nozzle and/or fixing device.

20 Claims, 8 Drawing Sheets

NOZZLE ARRANGEMENT

TECHNICAL FIELD

This invention relates to the nebulisation of liquids. In particular, though not exclusively, this invention relates to a nozzle arrangement for delivering a liquid from a liquid delivery device and to a liquid delivery device comprising the nozzle arrangement.

BACKGROUND

Drug delivery devices such as soft mist inhalers (SMIs) can be used to produce an aerosol of droplets for inhalation through the mouth and pharyngeal cavity into the lungs of a patient, for nasal administration, or for spraying the surface of the eye.

In an inhaler of this kind, liquid pharmaceutical formulations are typically stored in a reservoir. From there, they are conveyed through a riser tube into a pressure chamber from where they are forced through a nozzle under pressure and atomised. In this way, SMIs are able to nebulise a small amount of a liquid formulation according to the required dosage within a few seconds to produce an aerosol suitable for therapeutic inhalation. Moreover, this can be achieved without requiring the use of a propellant.

The nozzle is typically held in place in the device by a fixing means. As the liquid formulation is forced through the nozzle under pressure, a small amount of the liquid may be deposited as a film or as an accumulation of small droplets on the surface of the nozzle and/or the fixing means. It has been found that the deposited liquid can disrupt the flow of further liquid through the nozzle, which can affect the pharmaceutical quality of the aerosol mist.

Hence, there remains a need for improved drug delivery devices that can control the proportion and location/distribution of liquid deposited on the surface of the nozzle and/or the fixing means. It is an object of the invention to address at least one of the above problems, or another problem associated with the prior art.

SUMMARY OF THE INVENTION

A first aspect of the invention provides a nozzle arrangement for delivering a liquid from a liquid delivery device. The nozzle arrangement comprises a nozzle having an inlet side for receiving a liquid to be delivered and an outlet side for delivering the liquid. The nozzle arrangement also comprises a fixing device for fixing the nozzle in the delivery device and a recess located at or near the outlet side of the nozzle. The recess is arranged to wick away liquid deposited on the nozzle and/or fixing device.

It has been found that in such a nozzle arrangement, the recess may advantageously control liquid deposition on the outlet side of the nozzle and/or the fixing device by pulling any deposited liquid droplets away. This can reduce the amount of dispensed liquid deposited on the nozzle and/or fixing device and may thereby minimise or prevent disruption of the flow of further liquid through the nozzle. Significantly, this may allow for greater consistency of drug delivery from a delivery device comprising the nozzle arrangement through improved retained droplet control.

Suitably, the recess may be arranged to wick away liquid deposited on the nozzle and/or fixing device by capillary action. In this way, the recess may advantageously control liquid deposition on the outlet side of the nozzle and/or the fixing device by drawing any deposited liquid droplets away by capillary action.

In some embodiments, the nozzle arrangement may be suitable for delivering a liquid from a inhaler. Suitably, the liquid may be a pharmaceutical liquid. The term "pharmaceutical liquid" as defined herein refers to a solution, emulsion, or suspension of one or more active pharmaceutical ingredients in a suitable solvent. The inhaler may, for example, be a soft mist inhaler (SMI). Thus, the liquid delivery device may be an inhaler for nebulising pharmaceutical liquids. For example, the liquid delivery device may suitably be a soft mist inhaler (SMI).

In some embodiments, the recess may be located in the fixing device. For example, the recess may define an indentation or cavity in a side or outer surface of the fixing device.

Suitably, the recess may be located between the fixing device and the nozzle. For example, the recess may be defined by a gap between the fixing device and the nozzle. In some embodiments, the nozzle may comprise one or more components. In this context, the recess may be defined by a gap between the fixing device and the one or more components of the nozzle.

In some embodiments, the recess may be defined by a generally chamfered or curved face or edge of the fixing device. For example, one or more sides of the recess may be defined by a generally chamfered or curved face or edge of the fixing device.

In some embodiments, the nozzle may comprise a generally conical shaped recess in a nozzle holder. The fixing device may suitably fix the nozzle holder in the delivery device.

In some embodiments, the recess may be located in the nozzle holder. For example, the recess may define an indentation or cavity in a side or outer surface of the nozzle holder.

Suitably, the recess may be located between the fixing device and the nozzle holder. For example, the recess may be defined by a gap between the fixing device and the nozzle holder.

In some embodiments, the recess may be defined by a generally chamfered or curved face or edge of the nozzle holder. For example, one or more sides of the recess may be defined by a generally chamfered or curved face or edge of the nozzle holder.

In some embodiments, the nozzle may comprise a nozzle chip. A "nozzle chip" as defined herein is a component having an inlet end and an outlet end connected by a plurality of microstructured channels. The inlet end of the nozzle chip may comprise a filtering structure, comprising one or more microstructured channels that are generally zig-zag shaped (i.e. form a generally zig-zag structure). In this way, the filtering structure may advantageously prevent any coarse debris from blocking the microstructured channels at the outlet end. The outlet end of the nozzle chip may comprise one or more spray jets. Where two or more spray jets are present, the geometries of the spray jets may suitably be arranged to cause two or more jets of liquid exiting the spray jets to impinge upon one another (i.e. collide with each other).

Suitably, the recess may be located in the nozzle chip. For example, the recess may define an indentation or cavity in a side or outer surface of the nozzle chip.

In some embodiments, the nozzle holder may fix the nozzle chip in the delivery device. In such embodiments, the recess may be located between the nozzle holder and the nozzle chip. For example, the recess may be defined by a gap between the nozzle holder and the nozzle chip.

In some embodiments, the fixing device may directly fix the nozzle chip in the delivery device. In such embodiments, the recess may be located between the fixing device and the nozzle chip. For example, the recess may be defined by a gap between the fixing device and the nozzle chip.

In some embodiments, the recess may be defined by a generally chamfered or curved face or edge of the nozzle chip. For example, one or more sides of the recess may be defined by a generally chamfered or curved face or edge of the nozzle chip.

In some embodiments, the recess may be generally square or rectangular in cross-section. For example, the recess may define a ring (or partial ring segment) having a generally square or rectangular cross-section. In this context, the recess may define a generally square or rectangular cross-section following a curved or sweeping path. In some embodiments, the recess may be generally cuboidal in shape. Suitably, the recess may define a cuboidal shape having a curved or sweeping path.

In some embodiments, the recess may have an opening defined by a first width and/or a first length of the recess. In some embodiments, the first width and/or first length may define a plane of the opening. The plane of the opening may be generally flat or curved. Suitably, the recess may have a depth substantially orthogonal (i.e. generally 90°) to the plane of the opening.

In some embodiments, the recess may be generally square or rectangular in cross-section and located between the fixing device and the nozzle. For example, the recess may be generally square or rectangular in cross-section and located between the fixing device and the nozzle holder or between the fixing device and the nozzle chip.

In such embodiments, first and second surfaces of the nozzle may define first and second sides of the recess. The first surface of the nozzle may be at a right angle (i.e. 90°) to the second surface of the nozzle. A surface of the fixing device may define a third side of the recess opposite to the first side of the recess defined by the first surface of the nozzle. The surface of the fixing device may meet or join the second surface of the nozzle to form a right angle (i.e. 90°) therebetween. The first surface of the nozzle may end at a corner or edge of the nozzle. The surface of the fixing device may end at a corner or edge of the fixing device.

In some embodiments, the first and third sides of the recess may be of equal length. In such embodiments, a line drawn between the corner or edge of the nozzle and the corner or edge of the fixing device may define the width of the plane of the opening. In such embodiments, the depth of the recess may be defined by the length of the first (or third) side of the recess.

In some embodiments, the first side of the recess may be greater in length than the third side of the recess. In such embodiments, a line drawn at a right angle (i.e. 90°) to the surface of the fixing device between the corner or edge of the fixing device and the surface of the nozzle may define the width of the plane of the opening. In such embodiments, the depth of the recess may be defined by the length of the third side of the recess.

In some embodiments, the third side of the recess may be greater in length than the first side of the recess. In such embodiments, a line drawn at a right angle (i.e. 90°) to the surface of the nozzle between the corner or edge of the nozzle and the surface of the fixing device may define the width of the plane of the opening. In such embodiments, the depth of the recess may be defined by the length of the first side of the recess.

In some embodiments, the recess may be generally square or rectangular in cross-section and located between the nozzle chip and the nozzle holder. In such embodiments, first and second surfaces of the nozzle holder may define first and second sides of the recess. The first surface of the nozzle holder may be at a right angle (i.e. 90°) to the second surface of the nozzle holder.

A surface of the nozzle chip may define a third side of the recess opposite to the first side of the recess defined by the first surface of the nozzle holder. The surface of the nozzle chip may meet or join the second surface of the nozzle holder to form a right angle (i.e. 90°) therebetween. The first surface of the nozzle holder may end at a corner or edge of the nozzle holder. A line drawn at a right angle (i.e. 90°) to the first surface of the nozzle holder between the corner or edge of the nozzle holder and the surface of the nozzle chip may define the width of the plane of the opening. In such embodiments, the depth of the recess may be defined by the length of the first side of the recess.

In some embodiments, the recess may be generally circular in cross-section. For example, the recess may define a ring (or partial ring segment) having a generally circular cross-section. In some embodiments, the recess may be generally cylindrical in shape. Suitably, the recess may define a toroidal ring (or toroidal ring segment).

In some embodiments, the recess may be generally triangular in cross-section. For example, the recess may define a ring (or partial ring segment) having a generally triangular cross-section. Such a shape of the recess may advantageously increase the wicking away of liquid deposited on the nozzle and/or fixing device (for example, by capillary action). Conveniently, one or more angles may be added to a radial face of the nozzle and/or fixing device to create a recess having a triangular cross-section. In some embodiments, the recess may be wedge shaped. For example, the recess may be generally triangular prism shaped. Conveniently, one or more angles may be added to a radial face of the nozzle and/or fixing device to create a wedge shaped or triangular prism shaped recess.

In some embodiments, the recess may be generally triangular in cross-section and located between the fixing device and the nozzle. For example, the recess may be generally triangular in cross-section and located between the fixing device and the nozzle holder or between the fixing device and the nozzle chip.

In such embodiments, a surface of the nozzle may define a first side of the recess and a surface of the fixing device may define a second side of the recess. The surface of the nozzle and the surface of the fixing device may gradually come closer together until they meet or join together, thereby defining an angle (θ) between them. The surface of the fixing device may end at a corner or edge of the fixing device. The surface of the nozzle may extend out of the recess, for example, in a continuous plane.

A line drawn at a right angle (i.e. 90°) to the surface of the fixing device between the corner or edge of the fixing device and the surface of the nozzle may define the width of the plane of the opening. In this way, the first side of the recess may define the hypotenuse of a triangle, the second side of the recess may define the adjacent side of the triangle and the line drawn between the corner or edge of the fixing device and the surface of the nozzle defining the width of the plane of the opening may define the opposite side of the triangle.

In such embodiments, the length of the plane of the opening may be orthogonal to the width of the plane of the opening. Moreover, the depth of the recess may be defined by the length of the first side of the recess (i.e. by the length of the adjacent side of the triangle).

In some embodiments, the recess may be generally triangular in cross-section and located between the nozzle holder and the nozzle chip. In such embodiments, a surface of the nozzle holder may define a first side of the recess and a surface of the nozzle chip may define a second side of the recess. The surface of the nozzle chip and the surface of the nozzle holder may gradually come closer together until they meet or join together, thereby defining an angle (θ) between them. The surface of the nozzle holder may end at a corner or edge of the nozzle holder. The surface of the nozzle chip may extend out of the recess, for example, in a continuous plane.

A line drawn at a right angle (i.e. 90°) to the surface of the nozzle chip between the corner or edge of the nozzle holder and the surface of the nozzle chip may define the width of the plane of the opening. In this way, the first side of the recess may define the hypotenuse of a triangle, the second side of the recess may define the adjacent side of the triangle and the line drawn between the corner or edge of the nozzle holder and the surface of the nozzle chip defining the width of the plane of the opening may define the opposite side of the triangle.

In such embodiments, the length of the plane of the opening may be orthogonal to the width of the plane of the opening. Moreover, the depth of the recess may be defined by the length of the second side of the recess (i.e. by the length of the adjacent side of the triangle).

In some embodiments, the recess may be generally trapezoidal in cross-section. For example, the recess may define a ring (or partial ring segment) having a generally trapezoidal cross-section. Such a shape of the recess may advantageously increase the wicking away of liquid deposited on the nozzle and/or fixing device (for example, by capillary action). Conveniently, one or more angles may be added to a radial face of the nozzle and/or fixing device to create a recess having a trapezoidal cross-section. In some embodiments, the recess may be the recess may be generally trapezium or trapezoidal prism shaped. Conveniently, one or more angles may be added to a radial face of the nozzle and/or fixing device to create a trapezium or trapezoidal prism shaped recess.

In some embodiments, the recess may be generally curved in cross-section. For example, the recess may define a ring (or partial ring segment) having a generally curved cross-section.

Suitably, the recess may comprise opposing first and second sides. In some embodiments, one or both of the first and second sides may be generally curved.

In some embodiments, the first width of the recess may be in a range of from 0.1 mm to 5 mm. For example, the first width of the recess may be in a range of from 0.1 mm to 4 mm, or from 0.1 mm to 3 mm, or from 0.1 mm to 2 mm, or from 0.1 mm to 1 mm. Suitably, the first width of the recess may be in a range of from 0.5 mm to 5 mm, or from 0.5 mm to 4 mm, or from 0.5 mm to 3 mm, or from 0.5 mm to 2 mm, such as from 0.5 mm to 1 mm.

In some embodiments, the first width may narrow in a direction of the depth away from the opening. For example, the first width may be 5 mm and may narrow to a second width of 0.1 mm. In this context, the second width may define the width of the recess at its deepest point. Suitably, the first width may be 4 mm and may narrow to a second width of 0.1 mm, or the first width may be 3 mm and may narrow to a second width of 0.1 mm, or the first width may be 2 mm and may narrow to a second width of 0.1 mm, or the first width may be 1 mm and may narrow to a second width of 0.1 mm.

In some embodiments, the first width may be 5 mm and may narrow to a second width of 1 mm, or the first width may be 4 mm and may narrow to a second width of 1 mm, or the first width may be 3 mm and may narrow to a second width of 1 mm, or the first width may be 2 mm and may narrow to a second width of 1 mm.

In some embodiments, the width may narrow to zero in the direction of the depth away from the opening. For example, two opposing sides of the recess may gradually come closer together until they meet or join together. Thus, in this context, the second width may be zero.

In some embodiments, the depth of the recess may be in a range of from 0.1 to 1 mm, such as from 0.5 mm to 1 mm. For example, the depth of the recess may be in a range of from 0.1 mm to 2 mm, or from 0.1 mm to 3 mm, or from 0.1 mm to 4 mm, or from 0.1 mm to 5 mm, or from 0.1 mm to 6 mm, or from 0.1 mm to 7 mm, or from 0.1 mm to 8 mm, or from 0.1 mm to 9 mm, or even from 0.1 mm to 10 mm. In some embodiments, the depth of the recess may be in a range of from 0.5 mm to 2 mm, or from 0.5 mm to 3 mm, or from 0.5 mm to 4 mm, or from 0.5 mm to 5 mm, or from 0.5 mm to 6 mm, or from 0.5 mm to 7 mm, or from 0.5 mm to 8 mm, or from 0.5 mm to 9 mm, or even from 0.5 mm to 10 mm.

Suitably, the depth of the recess may be in a range of from 1 mm to 1.5 mm, or from 1 mm to 2 mm, or from 1 mm to 3 mm, or from 1 mm to 4 mm, or from 1 mm to 5 mm, or from 1 mm to 6 mm, or from 1 mm to 7 mm, or from 1 mm to 8 mm, or from 1 mm to 9 mm. For example, the depth of the recess may be about 0.5 mm, or about 1 mm, or about 2 mm, or about 3 mm, or about 4 mm, or about 5 mm, or about 6 mm, or about 7 mm, or about 8 mm, or about 9 mm, or even about 10 mm.

Increasing the depth of the recess may advantageously increase the volume of liquid that the recess is able to hold.

The nozzle may have a cylindrical axis substantially orthogonal (i.e. 90°) to a circumference of the nozzle. For example, the nozzle may have a cylindrical axis substantially orthogonal (i.e. 90°) to a circumference of the conical shaped recess of the nozzle. For embodiments in which the nozzle comprises a nozzle chip, the cylindrical axis may suitably be defined by a line between the inlet and outlet ends of the nozzle chip.

The circumference of the nozzle may be generally parallel to the plane of the outlet side (i.e. the outlet face) of the nozzle. For example, the circumference of the nozzle may be in the same plane as the plane of the outlet side (i.e. outlet face). In some embodiments, the depth of the recess may be generally parallel to the cylindrical axis of the nozzle. For example, the depth of the recess may be substantially orthogonal to the plane of the circumference of the nozzle.

In some embodiments, the depth of the recess may be substantially orthogonal (i.e. generally 90°) to the cylindrical axis of the nozzle. For example, the depth of the recess may be generally parallel to the plane of the circumference of the nozzle.

In some embodiments, the recess may have a length that extends at least partially along a circumference of the nozzle. For example, the recess may have a length that extends at least 10%, or at least 20%, or at least 30%, or at least 40%, or at least 60%, or at least 70%, or at least 80%, or at least 90%, or even at least 95% along the circumference of the nozzle. In this way, the recess may define a partial ring segment.

In some embodiments, the nozzle arrangement may comprise two or more separate recesses that extend at least partially along the circumference of the nozzle. In such embodiments, each of two or more recesses may have a length that extends less than 50%, or less than 40%, or less than 30%, or less than 20%, or less than 10%, or even less than 5% along the circumference of the nozzle. In this way, the two or more separate recesses may each define partial ring segments. Each of the two or more recesses may have different dimensions (e.g. length, width and depth) and may be orientated differently (e.g. relative to the cylindrical axis of the nozzle.

In some embodiments, the recess may have a length that defines a continuous loop extending along a circumference of the nozzle. For example, the recess may have a length that defines a complete loop extending along a circumference of the nozzle. In this way, the recess may define a ring.

In some embodiments, the recess may have a first width defined as the maximum width at which a meniscus of deionised water can be held in the recess and overcome gravity (i.e. when the recess is inverted such that the opening of the recess is orientated downwards so that it faces the floor/ground) at standard temperature and pressure, i.e. a temperature of 273.15 K (0° C.) and absolute pressure of 100 kPa (1 bar).

In this way, the maximum width at which a meniscus of deionised water can be held in the recess and overcome gravity may suitably define the maximum volume of deionised water that can be held in the recess at standard temperature and pressure.

In some embodiments, the maximum volume of deionised water that can be held in the recess at standard temperature and pressure may be in the range of from 1 to 7 μL, or in the range of from 2 to 8 μL, or in the range of from 3 to 9 μL, or in the range of from 4 to 10 μL, or in the range of from 5 to 11 μL, or in the range of from 6 to 12 μL, or in the range of from 7 to 13 μL, or in the range of from 8 to 14 μL, or in the range of from 9 to 15 μL, or in the range of from 10 to 16 μL, or in the range of from 11 to 17 μL, or in the range of from 12 to 18 μL, or in the range of from 13 to 19 μL, or in the range of from 14 to 20 μL, or in the range of from 15 to 21 μL, or in the range of from 16 to 22 μL, or in the range of from 17 to 23 μL, or in the range of from 18 to 24 μL, or in the range of from 19 to 25 μL, or in the range of from 20 to 26 μL, or in the range of from 21 to 27 μL, or in the range of from 22 to 28 μL, or in the range of from 23 to 29 μL, such as in the range of from 24 to 30 μL.

For example, the maximum volume of deionised water that can be held in the recess at standard temperature and pressure may be about 1 μL, or about 2 μL, or about 3 μL, or about 4 μL, or about 5 μL, or about 6 μL, or about 7 μL, or about 8 μL, or about 9 μL, or about 10 μL, or about 11 μL, or about 12 μL, or about 13 μL, or about 14 μL, or about 15 μL, or about 16 μL, or about 17 μL, or about 18 μL, or about 19 μL, or about 20 μL, or about 21 μL, or about 22 μL, or about 23 μL, or about 24 μL, or about 25 μL, or about 26 μL, or about 27 μL, or about 28 μL, or about 29 μL, or even about 30 μL.

In some embodiments, the fixing device may suitably comprise a nut.

Suitable materials for the nozzle and/or fixing device may include, but are not limited to, polyether ether ketone (PEEK), stainless steel and/or polyoxymethylene (POM).

A second aspect of the invention provides a liquid delivery device comprising a nozzle arrangement according to the first aspect of the invention.

The liquid delivery device may suitably be an inhaler for nebulising pharmaceutical liquids. For example, the liquid delivery device may suitably be a soft mist inhaler (SMI).

Throughout the description and claims of this specification, the words "comprise" and "contain" and variations of the words, for example "comprising" and "comprises", mean "including but not limited to", and do not exclude other components, integers or steps. Moreover, the singular encompasses the plural unless the context otherwise requires: in particular, where the indefinite article is used, the specification is to be understood as contemplating plurality as well as singularity, unless the context requires otherwise.

Preferred features of each aspect of the invention may be as described in connection with any of the other aspects. Within the scope of this application it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible.

BRIEF DESCRIPTION OF THE DRAWINGS

One or more embodiments of the invention will now be described, by way of example only, with reference to the accompanying drawings, in which.

DETAILED DESCRIPTION

Figure 1A:
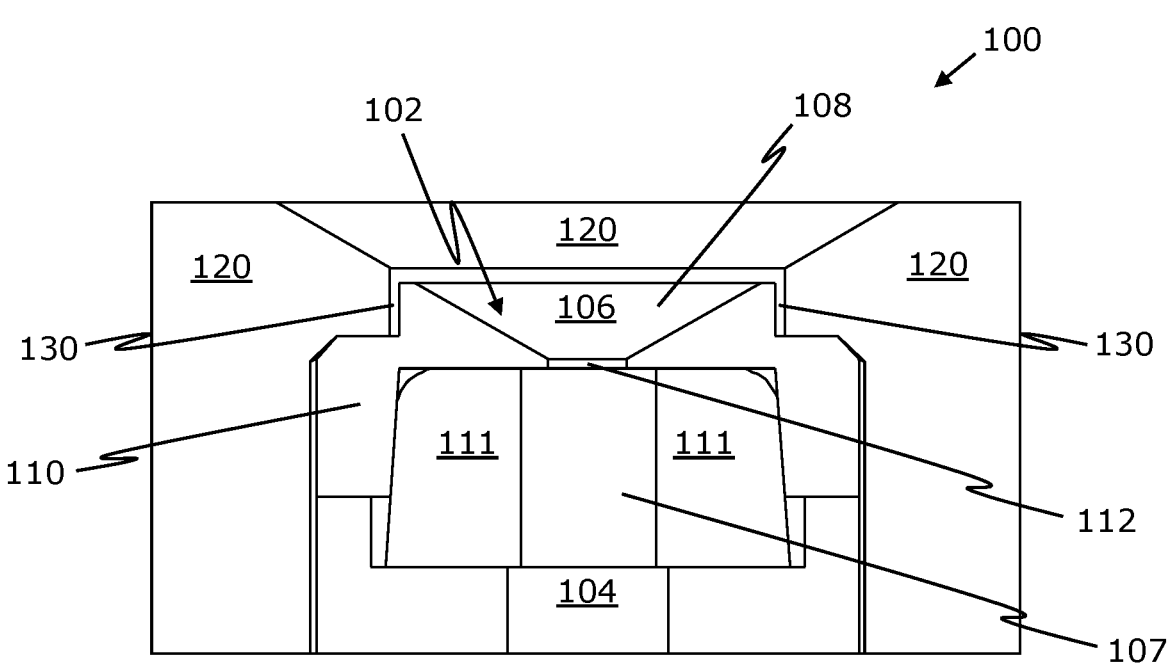
FIG. 1A is a cross-sectional view of a nozzle arrangement in accordance with a first embodiment of the invention.

Referring to FIG. 1A, a nozzle arrangement 100 in accordance with a first embodiment of the invention comprises a nozzle 102 having an inlet side 104 for receiving a liquid to be delivered and an outlet side 106 for delivering the liquid. The nozzle 102 comprises a nozzle chip 107 and a generally conical shaped recess 108 in a nozzle holder 110. The nozzle chip 107 is surrounded by an annular elastomeric seal 111. The nozzle holder 110 has a central aperture 112 for allowing the flow of liquid to exit through the nozzle holder 110 from the nozzle chip 107.

Figure 1B:
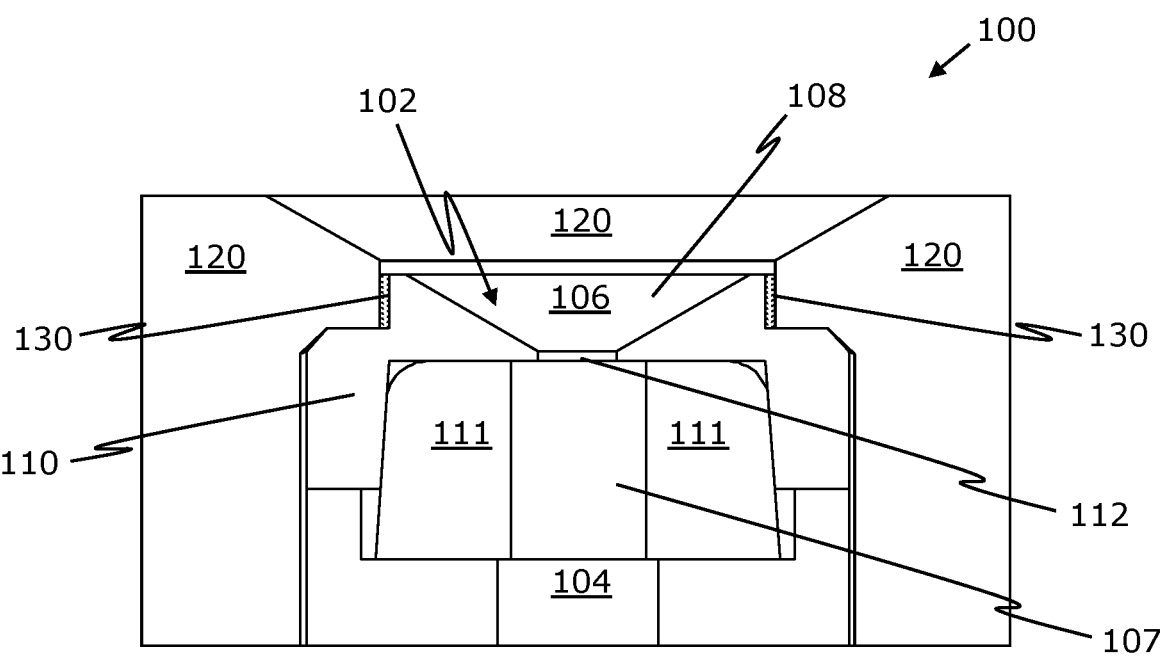
FIG. 1B is a cross-sectional view of the nozzle arrangement of FIG. 1A in which the recess is highlighted.

The nozzle arrangement 100 also comprises a nut 120 for fixing the nozzle holder 110 in place in a delivery device (not shown). A recess 130 is arranged between the nozzle holder 110 and the nut 120, In this example, the recess 130 is rectangular in cross-section, and has a length that extends the whole way round the circumference of the nozzle 102 to form a continuous loop (i.e. ring). The recess 130 has a depth that extends generally parallel to the cylindrical axis of the nozzle 120, as shown in FIG. 1B, in which the recess 130 is highlighted as a shaded area.

In use, liquid is forced under pressure through the nozzle chip 107 and out through the aperture 112 of the nozzle holder 110 from the inlet side 104 to the outlet side 106. As the liquid exits the aperture 112 it is atomised to form an aerosol mist, which is directed away from the aperture 112 through the conical shaped recess 108. During atomisation, a small amount of the liquid may be deposited on the surfaces of the conical shaped recess 108, the nozzle holder 110 and/or the nut 120 on the outlet side 106, for example, as an accumulation of small droplets.

The deposited liquid is wicked away by the recess 130, for example, by capillary action. This reduces the amount of liquid deposited on the surfaces of the conical shaped recess 108, the nozzle holder 110 and/or nut 120 on the outlet side 106, thereby minimising or preventing disruption of the flow of further liquid exiting the nozzle chip 107 through the aperture 112.

Figure 2:
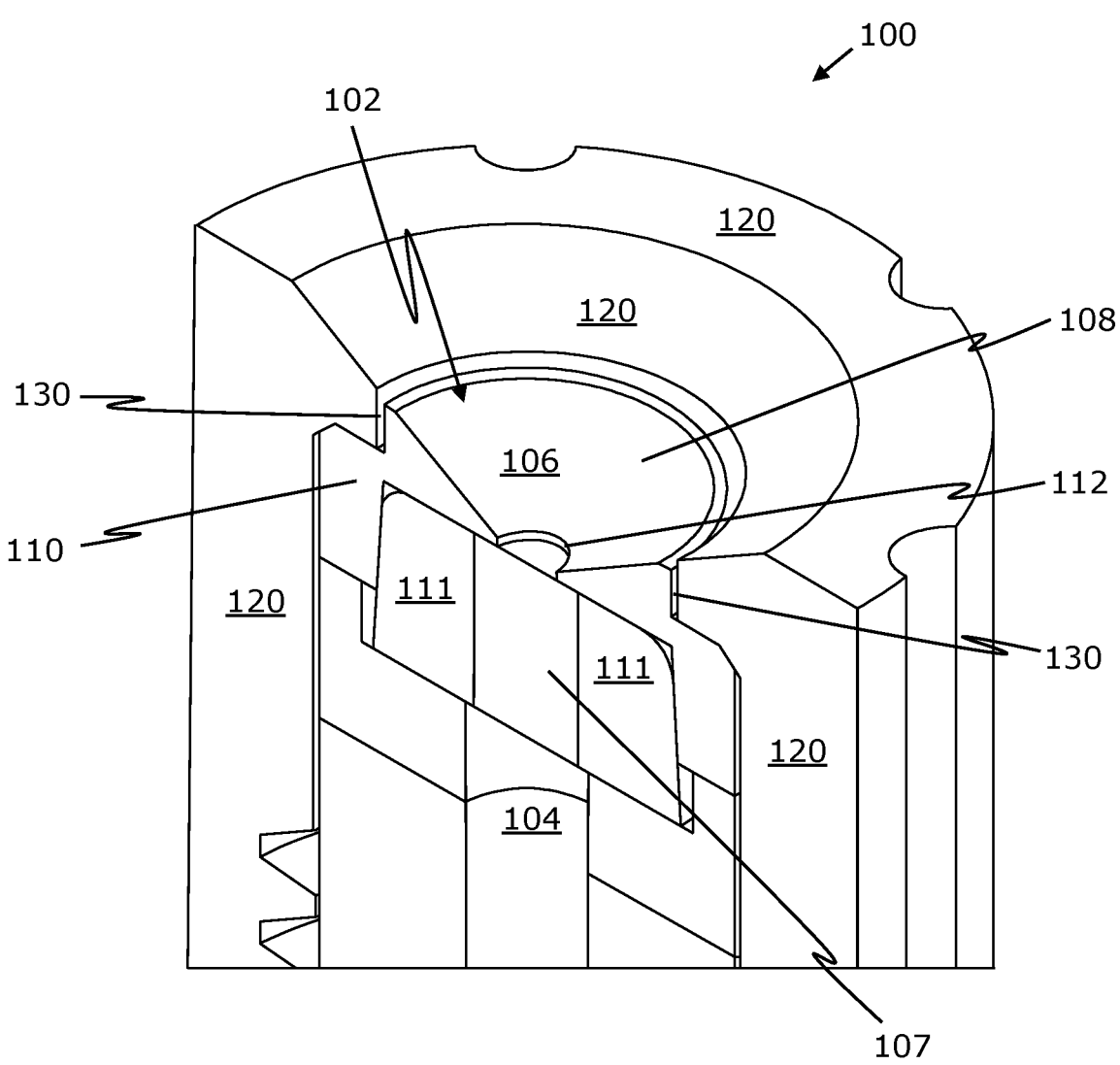
FIG. 2 is a cross-sectional perspective view of the nozzle arrangement of FIG. 1A inside a liquid delivery device.
Figure 3:
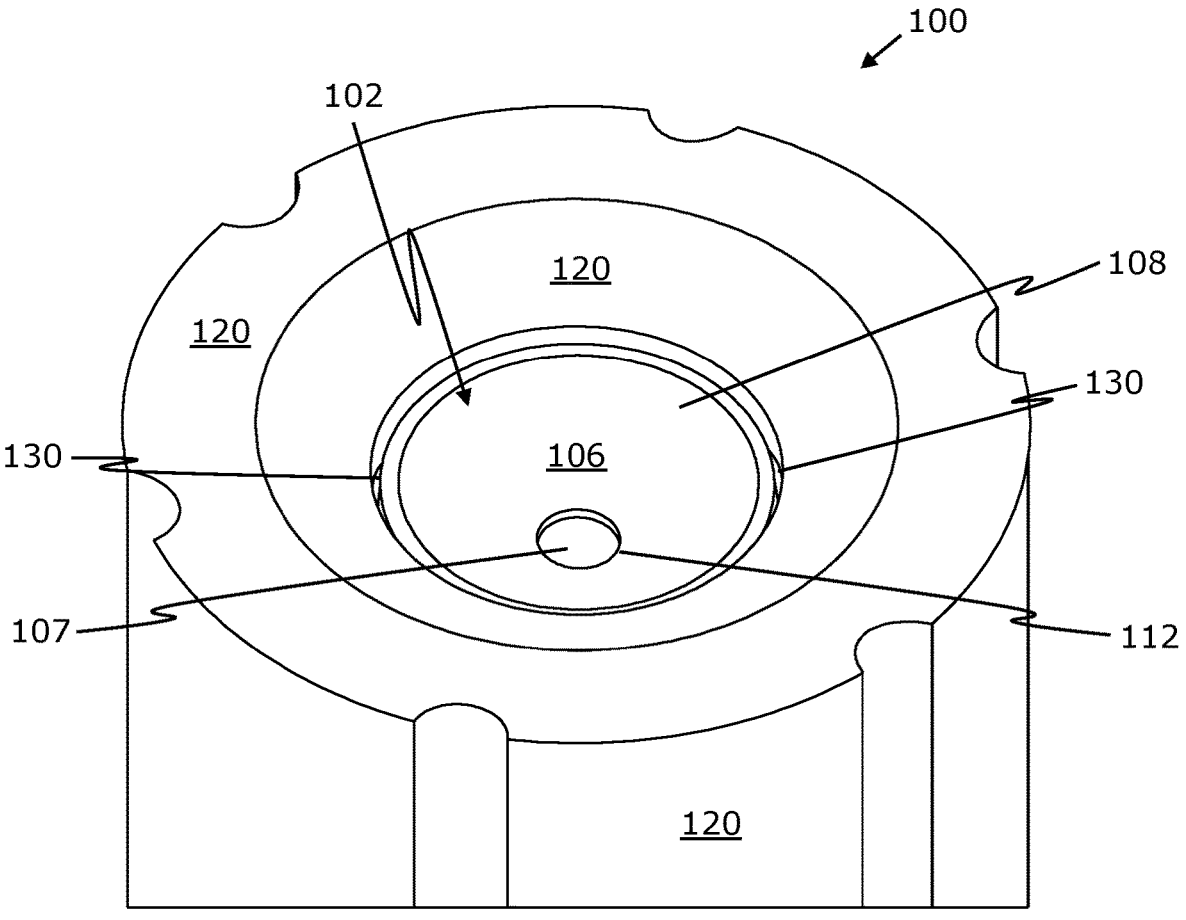
FIG. 3 is a perspective view of the nozzle arrangement of FIG. 1A inside a liquid delivery device.

FIG. 2 shows a cross-sectional perspective view of the nozzle arrangement 100. FIG. 3 shows a perspective view of the nozzle arrangement 100.

Figure 4:
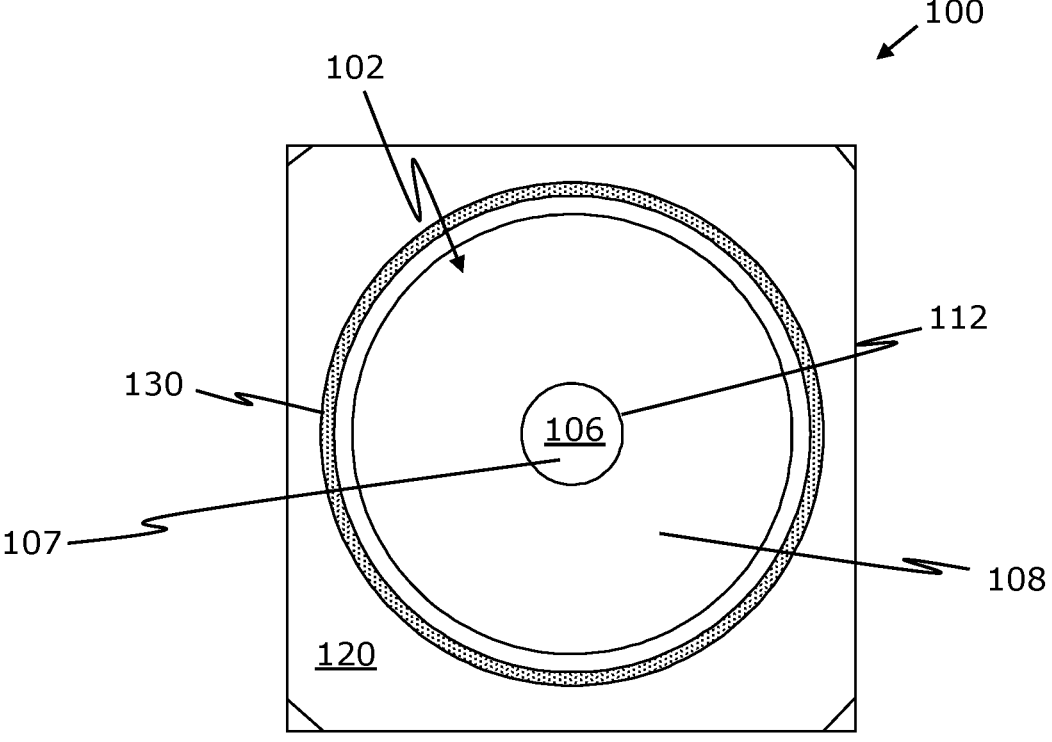
FIG. 4 is a top view of the nozzle arrangement of FIG. 1A in which the recess is highlighted.

FIG. 4 shows a top view of the nozzle arrangement 100, in which the recess is highlighted as a shaded area. As can be seen from FIG. 4, the recess 130 has a length that extends the whole way round the circumference of the nozzle 102 to form a continuous loop (i.e. ring).

Figure 5:
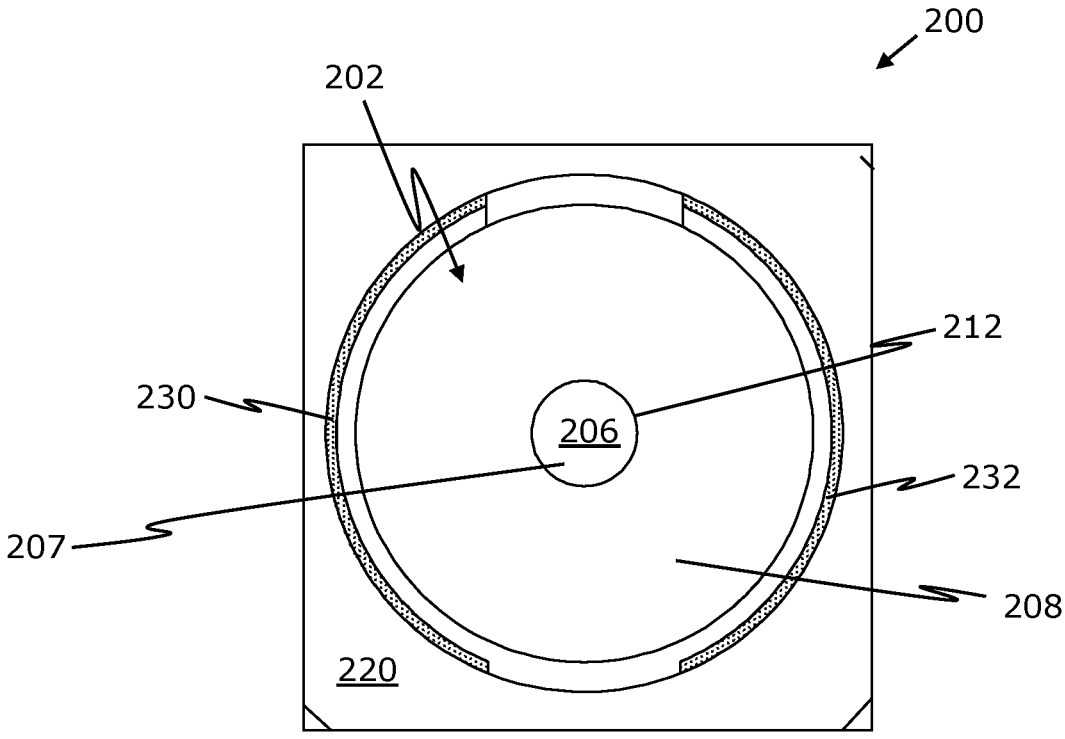
FIG. 5 is a top view of a nozzle arrangement in accordance with a second embodiment of the invention in which the recess is highlighted.

FIG. 5 shows a top view of a nozzle arrangement 200 in accordance with a second embodiment of the invention. The nozzle arrangement 200 is similar to the nozzle arrangement 100 in accordance with the first embodiment of the invention, comprising a nozzle 202 having an inlet side 204 (not visible in FIG. 5) for receiving a liquid to be delivered and an outlet side 206 for delivering the liquid. The nozzle 202 comprises nozzle chip 207 and a generally conical shaped recess 208 in a nozzle holder 210. The nozzle holder 210 has a central aperture 212 for allowing the flow of liquid to exit through the nozzle holder 210 from the nozzle chip 207.

The nozzle arrangement 200 also comprises a nut 220 for fixing the nozzle holder 210 in place in a delivery device (not shown). First and second recesses 230, 232 are arranged between the nozzle holder 210 and the nut 220. In this example, each of the recesses 230, 232 are rectangular in cross-section, and have a length that extends about ⅜ of the way round the circumference of the nozzle 202 to form two separate partial ring segments separated at each end by about ⅛ of the circumference of the nozzle 202. Each of the recesses 230, 232 has a depth that extends generally parallel to the cylindrical axis of the nozzle 220.

Figure 6:
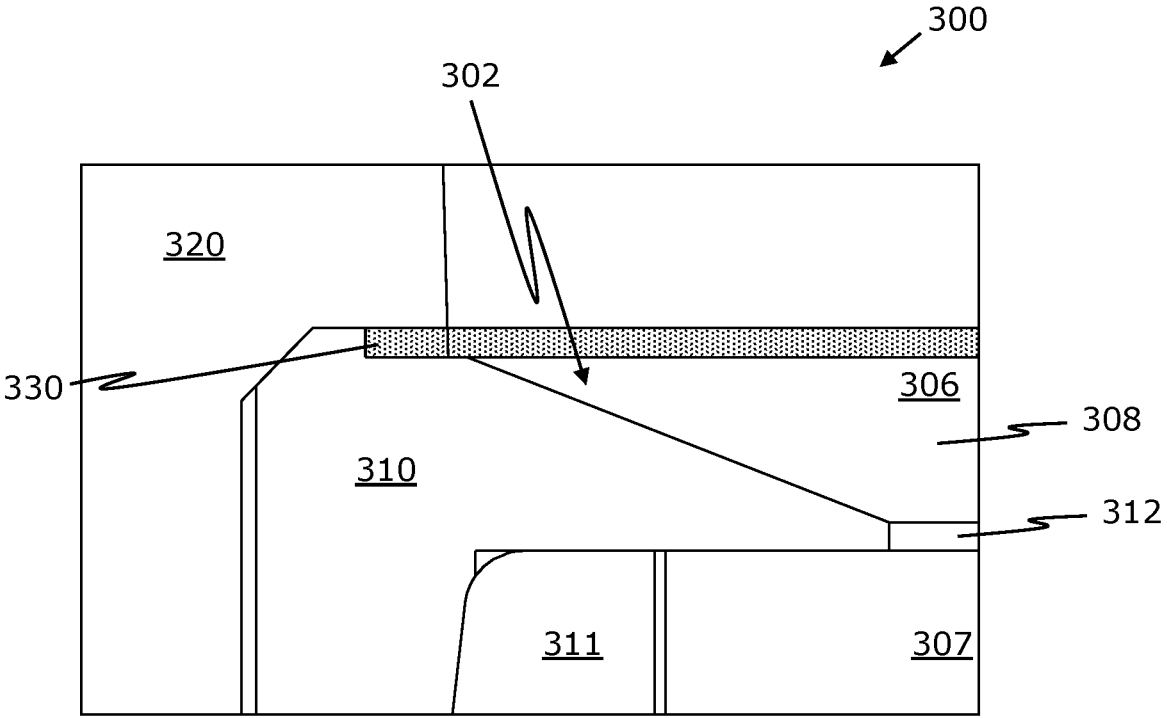
FIG. 6 is a cross-sectional view of a nozzle arrangement in accordance with a third embodiment of the invention.

Referring to FIG. 6, a nozzle arrangement 300 in accordance with a third embodiment of the invention comprises a nozzle 302 having an inlet side 304 (not shown) for receiving a liquid to be delivered and an outlet side 306 for delivering the liquid. The nozzle 302 comprises a nozzle chip 307 and a generally conical shaped recess 308 in a nozzle holder 310. The nozzle holder 310 has a central aperture 312 for allowing the flow of liquid to exit through the nozzle holder 310 from the nozzle chip 307.

The nozzle arrangement 300 also comprises a nut 320 for fixing the nozzle holder 310 in place in a delivery device (not shown). A recess 330 is arranged between the nozzle holder 310 and the nut 320, In this example, the recess 330 is rectangular in cross-section, and has a length that extends the whole way round the circumference of the nozzle 302 to form a continuous loop (i.e. ring). The recess 330 has a depth that extends generally orthogonal to the cylindrical axis of the nozzle 302, as shown in FIG. 6, in which the recess 330 is highlighted as a shaded area.

Figure 7:
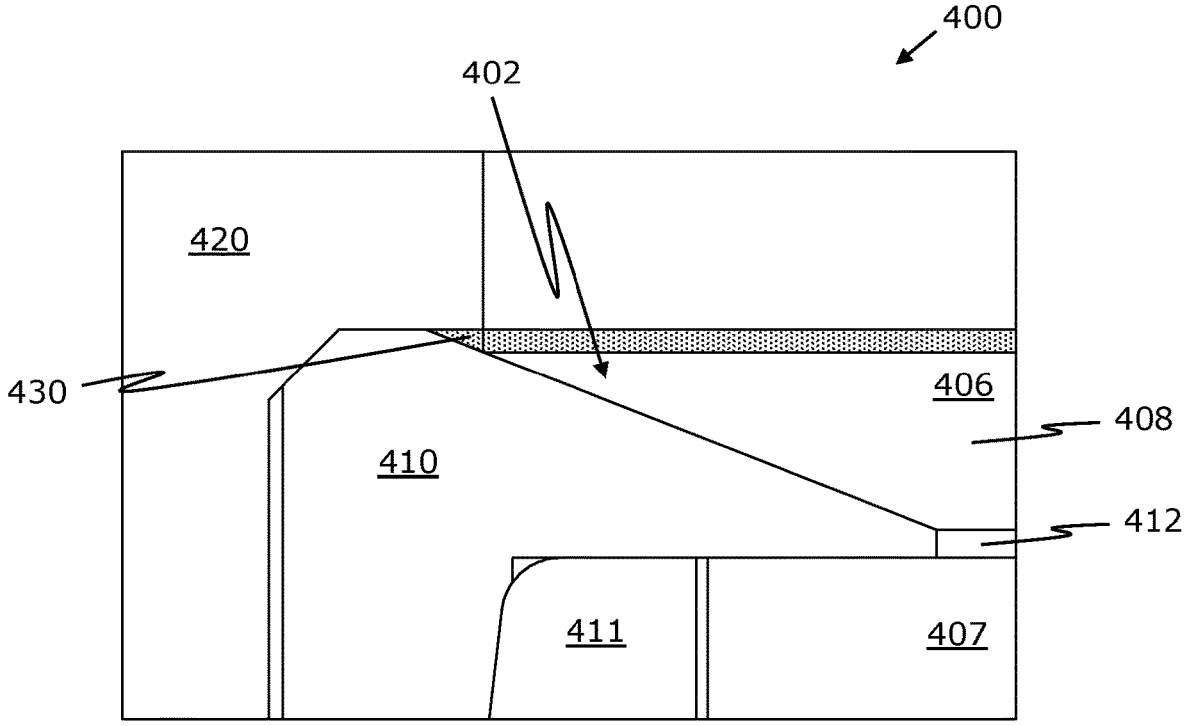
FIG. 7 is a cross-sectional view of a nozzle arrangement in accordance with a fourth embodiment of the invention.

Referring to FIG. 7, a nozzle arrangement 400 in accordance with a fourth embodiment of the invention comprises a nozzle 402 having an inlet side 404 (not shown) for receiving a liquid to be delivered and an outlet side 406 for delivering the liquid. The nozzle 402 comprises a nozzle chip 407 and a generally conical shaped recess 408 in a nozzle holder 410. The nozzle holder 410 has a central aperture 412 for allowing the flow of liquid to exit through the nozzle holder 410 from the nozzle chip 407.

The nozzle arrangement 400 also comprises a nut 420 for fixing the nozzle holder 410 in place in a delivery device (not shown). A recess 430 is arranged between the nozzle holder 410 and the nut 420. In this example, the recess 430 is triangular (i.e. wedge shaped) in cross-section, and has a length that extends the whole way round the circumference of the nozzle 402 to form a continuous loop (i.e. ring). The recess 430 has a depth that extends generally orthogonal to the cylindrical axis of the nozzle 402, as shown in FIG. 7, in which the recess 430 is highlighted as a shaded area.

Figure 8:
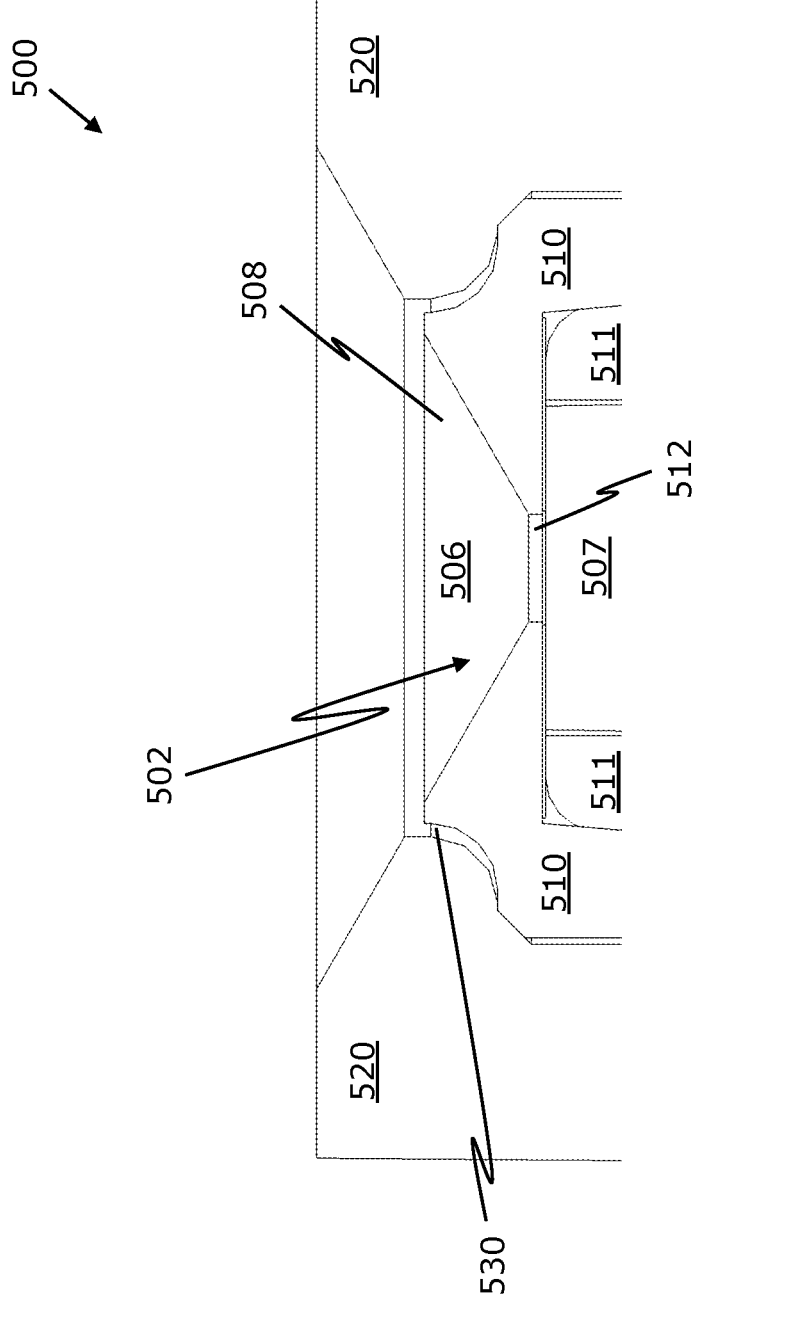
FIG. 8 is a cross-sectional view of a nozzle arrangement in accordance with a fifth embodiment of the invention.

Referring to FIG. 8, a nozzle arrangement 500 in accordance with a fifth embodiment of the invention comprises a nozzle 502 having an inlet side 504 (not shown) for receiving a liquid to be delivered and an outlet side 506 for delivering the liquid. The nozzle 502 comprises a nozzle chip 507 and a generally conical shaped recess 508 in a nozzle holder 510. The nozzle holder 510 has a central aperture 512 for allowing the flow of liquid to exit through the nozzle holder 510 from the nozzle chip 507.

The nozzle arrangement 500 also comprises a nut 520 for fixing the nozzle holder 510 in place in a delivery device (not shown). A recess 530 is arranged between the nozzle holder 510 and the nut 520. In this example, the recess 530 is curved in cross-section, and has a length that extends the whole way round the circumference of the nozzle 502 to form a continuous loop (i.e. ring). The recess 530 has a depth that extends away from the opening of the recess 520 in a direction generally parallel to the cylindrical axis of the nozzle 502 and gradually curves away such that the depth extends generally perpendicular to the cylindrical axis of the nozzle 502 at the lowermost end (i.e. the bottom) of the recess 530.

EXAMPLES

Comparative Example (Not in Accordance With the Invention)

A Malvern Panalytical® Spraytec™ laser diffraction system was used to observe the droplet diameters over a number of actuations (i.e. spay events) for a delivery device comprising a nozzle arrangement in accordance with the first embodiment of the invention, however, in which the recess was filled in (i.e. blocked). In this example, a high average Dv90 was observed, along with a high variability in the droplet size. The Dv90 value indicates that 90% of the spray volume is contained in droplets that are smaller than the Dv90 value, and 10% is contained in droplets that are larger than the Dv90 value. The high average Dv90 was attributed to droplets forming on the nozzle and running back into the path of the central aperture of the nozzle holder and disrupting the spray formed by the nozzle chip.

Example 1

A Malvern Panalytical® Spraytec™ laser diffraction system was used to observe the droplet diameters over a number of actuations (i.e. spay events) for a delivery device comprising the nozzle arrangement used in the comparative example above, however, in this example the wicking recess was not filled in (i.e. blocked). In this example, a lower average Dv90 was observed, with less variability in the size of droplets within an actuation and between actuations. The wicking recess was found to reduce the occurrence of droplets running back into the path of the central aperture of the nozzle holder and therefore reduce disruption to the spray formed by the nozzle chip. This resulted in less variability in the droplet sizes and a reduction in the average Dv90.

The invention claimed is:

1. A nozzle arrangement for delivering a liquid from an inhaler, comprising:
   a nozzle retained within a nozzle holder, the nozzle having an inlet side for receiving a liquid to be delivered and an outlet side for delivering the liquid;
   a fixing device configured to secure the nozzle holder in the inhaler during use; and
   at least one recess located at or near the outlet side of the nozzle, wherein the at least one recess is arranged to wick away liquid deposited on the nozzle and/or fixing device.

2. The nozzle arrangement of claim 1, wherein the at least one recess is located in the fixing device.

3. The nozzle arrangement of claim 1, wherein the at least one recess is located between the fixing device and the nozzle.

4. The nozzle arrangement of claim 3, wherein the at least one recess is defined by a chamfered or curved face of the fixing device.

5. The nozzle arrangement of claim 1, wherein the at least one recess is square or rectangular in cross-section.

6. The nozzle arrangement of claim 1, wherein the at least one recess is triangular or trapezoidal in cross-section.

7. The nozzle arrangement of claim 1, wherein the at least one recess has an opening defined by a first width and a first length of the at least one recess.

8. The nozzle arrangement of claim 7, wherein the first width and first length define a plane of the opening, and wherein the at least one recess has depth orthogonal to the plane of the opening.

9. The nozzle arrangement of claim 8, wherein the depth of the at least one recess is parallel to the cylindrical axis of the nozzle.

10. The nozzle arrangement of claim 8, wherein the depth of the at least one recess is orthogonal to the cylindrical axis of the nozzle.

11. The nozzle arrangement of claim 7, wherein the first width of the at least one recess is in a range of from 0.1 mm to 5 mm.

12. The nozzle arrangement of claim 7, wherein the first width narrows in the direction of the depth away from the opening.

13. The nozzle arrangement of claim 12, wherein the width narrows to zero in the direction of the depth away from the opening.

14. The nozzle arrangement of claim 7, wherein the depth of the at least one recess is in a range of from 0.5 mm to 10 mm.

15. The nozzle arrangement of claim 1, wherein the at least one recess has a length that extends at least partially along a circumference of the nozzle.

16. The nozzle arrangement of claim 1, wherein the at least one recess has a length that defines a continuous loop extending a circumference of the nozzle.

17. The nozzle arrangement of claim 1, wherein the fixing device comprises a nut.

18. A liquid delivery device comprising a nozzle arrangement according to claim 1.

19. The liquid delivery device of claim 18, being the inhaler for nebulising pharmaceutical liquids.

20. The liquid delivery device of claim 18, being a soft mist inhaler (SMI).

* * * * *